(12) United States Patent
Lee

(10) Patent No.: US 12,251,212 B2
(45) Date of Patent: *Mar. 18, 2025

(54) CAP-SHAPED PORTABLE STADIOMETER

(71) Applicant: Andrew Lee, Portland, OR (US)

(72) Inventor: Andrew Lee, Portland, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 18/816,981

(22) Filed: Aug. 27, 2024

(65) Prior Publication Data

US 2024/0415411 A1 Dec. 19, 2024

Related U.S. Application Data

(63) Continuation of application No. 18/764,046, filed on Jul. 3, 2024, which is a continuation of application No. 18/743,014, filed on Jun. 13, 2024.

(51) Int. Cl.
| | |
|---|---|
| *A61B 5/107* | (2006.01) |
| *G01B 3/04* | (2006.01) |
| *G01B 7/00* | (2006.01) |
| *G01B 7/06* | (2006.01) |
| *G01B 11/06* | (2006.01) |

(52) U.S. Cl.
CPC .............. *A61B 5/1072* (2013.01); *G01B 3/04* (2013.01); *G01B 7/002* (2013.01); *G01B 7/06* (2013.01); *G01B 11/0608* (2013.01)

(58) Field of Classification Search
CPC ........ A61B 5/1072; G01B 3/04; G01B 7/002; G01B 7/06; G01B 11/0608
See application file for complete search history.

(56) References Cited

U.S. PATENT DOCUMENTS

| | | | | |
|---|---|---|---|---|
| D243,835 | S  * | 3/1977 | Hutchinson | ..................... D10/71 |
| 4,518,052 | A  * | 5/1985 | Chen | ...................... G01G 19/50 |
| | | | | 250/202 |
| 6,237,239 | B1 * | 5/2001 | Miyazaki | .............. A61B 5/1072 |
| | | | | 33/757 |
| 6,599,045 | B1 * | 7/2003 | Kolb | ....................... B43K 29/18 |
| | | | | 33/389 |
| 6,847,586 | B1 * | 1/2005 | Chen | ........................ A42B 1/24 |
| | | | | 367/115 |
| 7,163,516 | B1 * | 1/2007 | Pagnacco | ............... A61B 3/032 |
| | | | | 600/595 |
| D611,368 | S  * | 3/2010 | Garthoff | ......................... D10/70 |
| 7,739,925 | B2 * | 6/2010 | Foster | ...................... A63G 4/00 |
| | | | | 73/865.8 |

(Continued)

*Primary Examiner* — Son T Le
*Assistant Examiner* — Tania Courson
(74) *Attorney, Agent, or Firm* — Renaissance IP Law Group LLP

(57) ABSTRACT

A stadiometer includes a cap portion to be worn on a head of a user; a connecting portion having a first end coupled to the cap portion and a measuring portion coupled to a second end of the connecting portion. The measuring portion includes a plurality of sensors and a measuring rod. The stadiometer also includes a height measuring plate contactable by the plurality of sensors and the measuring rod. The sensors and measuring rod are configured such that the measuring rod is horizontal when the height measuring plate is contacted by the plurality of sensors simultaneously. The measuring rod is configured to contact the height measuring plate when the height measuring plate is contacted by the plurality of sensors simultaneously.

2 Claims, 5 Drawing Sheets

(56) References Cited

U.S. PATENT DOCUMENTS

| | | | |
|---|---|---|---|
| 8,109,008 B1* | 2/2012 | Niemczak | A61B 5/1079 |
| | | | 600/587 |
| 8,322,043 B2* | 12/2012 | Cha | A61B 5/1072 |
| | | | 33/832 |
| 8,425,434 B2* | 4/2013 | Mulder | A01K 29/00 |
| | | | 119/51.01 |
| 8,869,415 B1* | 10/2014 | Haykeen | A61B 5/1072 |
| | | | 33/485 |
| 9,658,058 B1* | 5/2017 | Jones | G01B 21/02 |
| 2012/0189227 A1* | 7/2012 | Cohen | G06F 3/0383 |
| | | | 382/314 |
| 2024/0324901 A1* | 10/2024 | Lee | G01B 11/0608 |
| 2024/0366108 A1* | 11/2024 | Lee | G01B 7/002 |

* cited by examiner

CAP-SHAPED PORTABLE STADIOMETER

CROSS-REFERENCE TO RELATED APPLICATION

This application is a continuation of U.S. patent application Ser. No. 18/764,046, filed Jul. 3, 2024, which is a continuation of U.S. patent application Ser. No. 18/743,014, filed Jun. 13, 2024, the disclosure of which is incorporated herein by reference in its entirety.

BACKGROUND

1. Field

Embodiments of the present inventive concept relate to a cap-shaped portable stadiometer, and more specifically, to a stadiometer capable of determining the horizontality during measurement, enabling high precision.

2. Description of the Related Art

With the recent increase in interest in health, the healthcare industry has expanded, leading to a growing demand for height information, one of the indicators used in this field. However, conventional height measurement tools are bulky and less user-friendly for households compared to other electronic devices, despite the rising demand. Therefore, individuals in the high-growth stages, where changes in height are frequent, face difficulties in measuring their height at the desired times and in the available space.

In order to address this problem, the development of portable stadiometers has taken place; however, there is a challenge in achieving an accurate measurement due to the stadiometer not level with the ground or sensor malfunctions during height measurement.

Therefore, there is a need for the development of a portable stadiometer that allows for accurate height measurement while being convenient for storage and transport, making it easy to use.

SUMMARY

Embodiments of the present inventive concept have been made in an effort to solve the above-described problems associated with prior art, and an object of the present inventive concept is to provide a cap-shaped portable stadiometer comprising: a detachable cap portion in the form of a cap; a measuring portion including fiver protrusions and capable of measuring the horizontality and height; and a connecting portion connecting the cap portion and the measuring portion.

According to one embodiment of present inventive concept, a stadiometer can be broadly characterized as including a cap portion adapted to be worn on a head of a user; a connecting portion having a first end coupled to the cap portion and a measuring portion coupled to a second end of the connecting portion. The measuring portion includes a plurality of sensors and a measuring rod. The stadiometer also includes a height measuring plate contactable by the plurality of sensors and the measuring rod. The plurality of sensors and measuring rod are configured such that measuring rod is horizontal when the height measuring plate is contacted by the plurality of sensors simultaneously. The measuring rod is configured to contact the height measuring plate when the height measuring plate is contacted by the plurality of sensors simultaneously.

BRIEF DESCRIPTION OF THE DRAWINGS

The above and other features and advantages of embodiments of the present inventive concept will become more apparent by describing in detail exemplary embodiments thereof with reference to the attached drawings in which.

DETAILED DESCRIPTION

Figure 1:
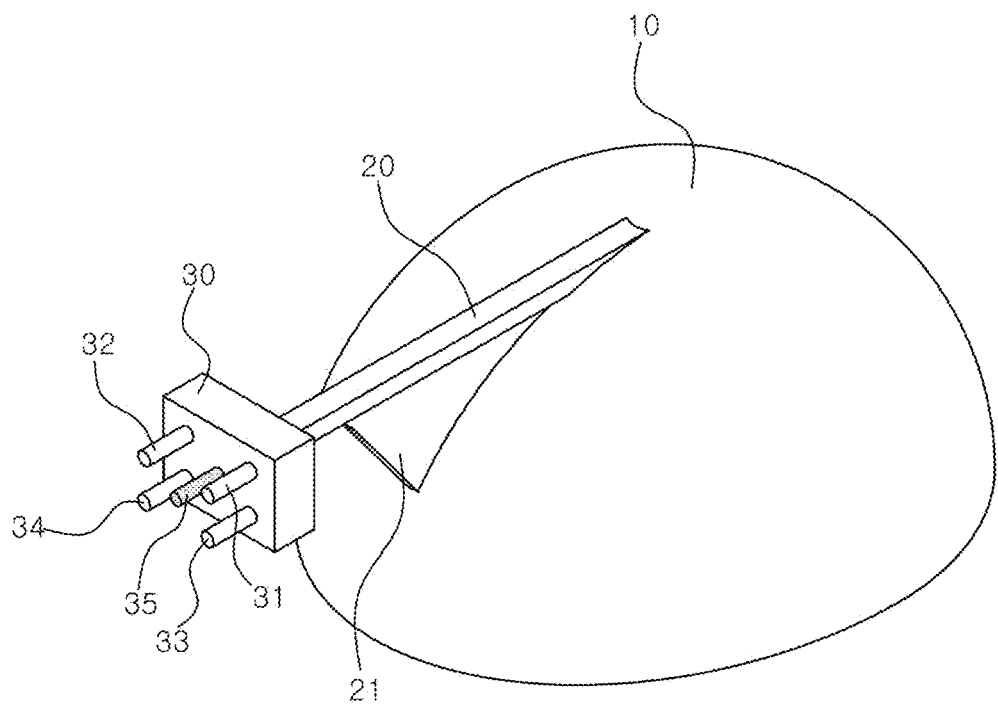
FIG. 1 is a perspective view illustrating a cap-shaped stadiometer according to a preferred embodiment of the present inventive concept.

As the present inventive concept allows for various changes and numerous embodiments, particular embodiments will be illustrated in the drawings and described in detail in the written description. However, this is not intended to limit the present inventive concept to particular modes of practice, and it is to be appreciated that all changes, equivalents, and substitutes that do not depart from the spirit and technical scope of the present inventive concept are encompassed in the present inventive concept.

Unless defined otherwise, all terms used herein including technical or scientific terms have the same meaning as those generally understood by those skilled in the art to which the present inventive concept pertains. It will be further understood that terms defined in dictionaries that are commonly used should be interpreted as having meanings that are consistent with their meanings in the context of the relevant art and should not be interpreted as having ideal or excessively formal meanings unless clearly defined in the present application.

Hereinafter, various s embodiments of the present inventive concept will be described in more detail with reference to the accompanying drawings.

EXAMPLES

Figure 2:
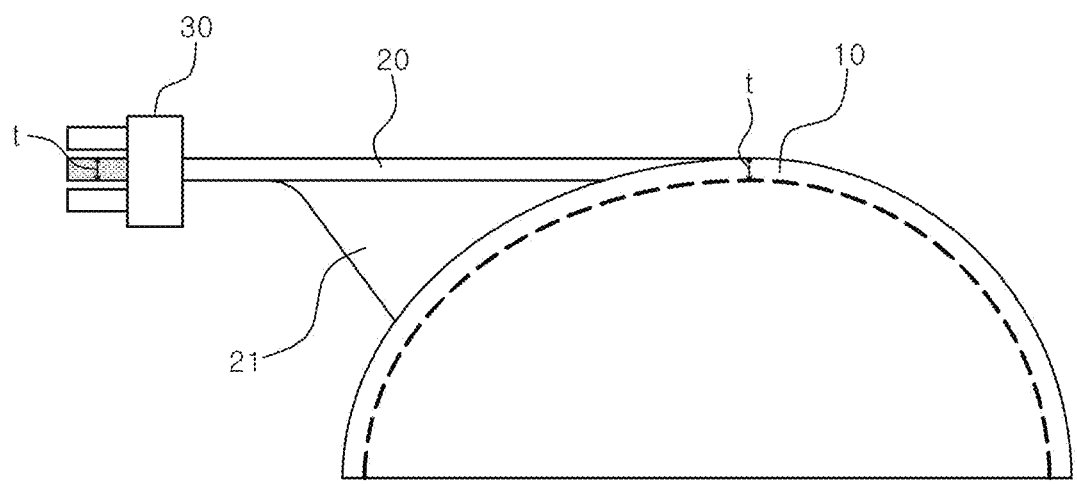
FIG. 2 is a side view schematically illustrating the cap-shaped stadiometer according to a preferred embodiment of the present inventive concept.
Figure 3:
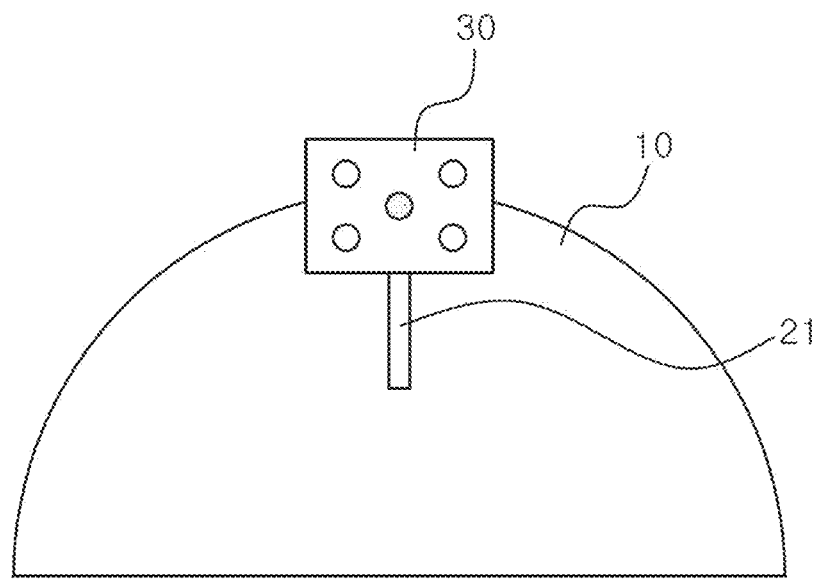
FIG. 3 is a front view schematically illustrating the cap-shaped stadiometer according to a preferred embodiment of the present inventive concept.

FIG. 1 is a perspective view illustrating a cap-shaped stadiometer according to a preferred embodiment of the present inventive concept, FIG. 2 is a side view schematically illustrating the cap-shaped stadiometer according to a preferred embodiment of the present inventive concept; and FIG. 3 is a front view schematically illustrating the cap-shaped stadiometer according to a preferred embodiment of the present inventive concept.

Referring to FIGS. 1 to 3, the stadiometer may comprise a cap portion 10, a connecting portion 20, and a measuring portion 30.

The cap portion 10 is configured in the form of a cap, making it easily detachable and suitable for wearing on the head of a user during height measurement.

The connecting portion 20 has a rod-shaped structure that connects the cap portion 10 and the measuring portion 30. One part of the connecting portion 20 is connected to the top of the cap portion 10 and is placed in a direction parallel to the ground. The opposite part of the connecting portion 20 is connected to the central part of the measuring portion 30. The cap portion 10 and the measuring portion 30 are connected through the connecting portion 20, allowing the height information of the cap portion 10 to be provided to the measuring portion 30. The connecting portion 20 is preferably made of plastic, but is not limited thereto, and any material that is rigid enough to maintain the horizontality will suffice.

The connecting portion 20 may further include a support 21 connected to the cap portion 10 for the stability of support. The support 21 is preferably made of the same material as the connecting portion 20, but is not limited thereto, and any hard material capable of supporting the connecting portion 20 will suffice. Moreover, the support 21 may be in the form of a rod or a flat structure connected to the cap portion 10 and the connecting portion 20, but is not limited thereto.

The measuring portion 30 has five protrusions, and these protrusions are composed of four sensors 31, 32, 33 and 34 and one measuring rod 35, all of which have the same length. These sensors 31, 32, 33 and 34 are capable of determining the horizontality. Since the sensors 31, 32, 33 and 34 have the same length, when all four sensors come into contact with a height measuring plate, the measuring portion 30 can be level with the ground. When all four sensors come into contact with the height measuring plate, light-emitting diodes provided on the height measuring plate emit light, making it easy to determine the horizontality.

The measuring rod 35 is located at the center of the measuring portion 30 and has the same height as the top of the cap portion 10. Referring again to FIG. 2, the width of the measuring rod 35 indicated by the arrow in FIG. 2 is the same as the cross-sectional thickness (t) of the cap portion 10 indicated by the arrow, which makes it possible to measure accurate height information that does not include the cross-sectional thickness (t) of the cap portion 10. The measuring rod 35 has the same length as the sensors 31, 32, 33 and 34, and thus only when all the sensors 31, 32, 33 and 34 come into contact with the height measuring plate to be level with the height measuring plate, the height measurement is possible. The measuring rod 35 may be either a stamp type, where ink is applied to the end thereof and printed on the height measuring plate, or a detachable type, where ink is loaded into the measuring rod 35 itself and extracted when it comes into contact with the height measuring plate, allowing for the display of height information.

Figure 4A:
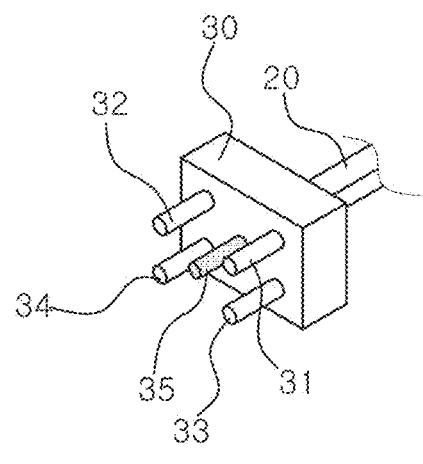
FIGS. 4($a$) and 4($b$) are diagrams illustrating a measuring portion according to a preferred embodiment of the present inventive concept and a circuit diagram of the measuring portion.
Figure 4B:
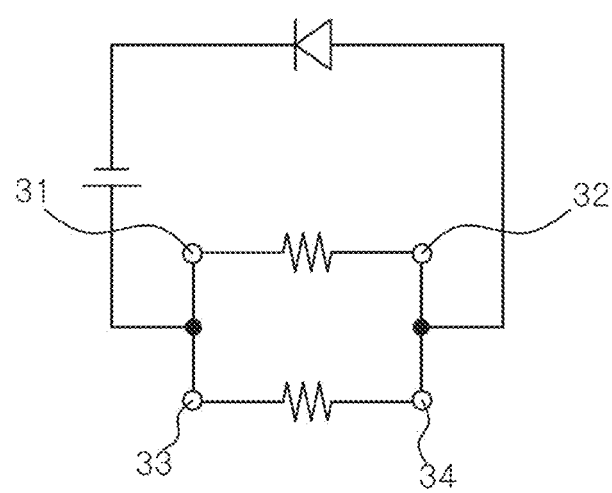
Figure 5:
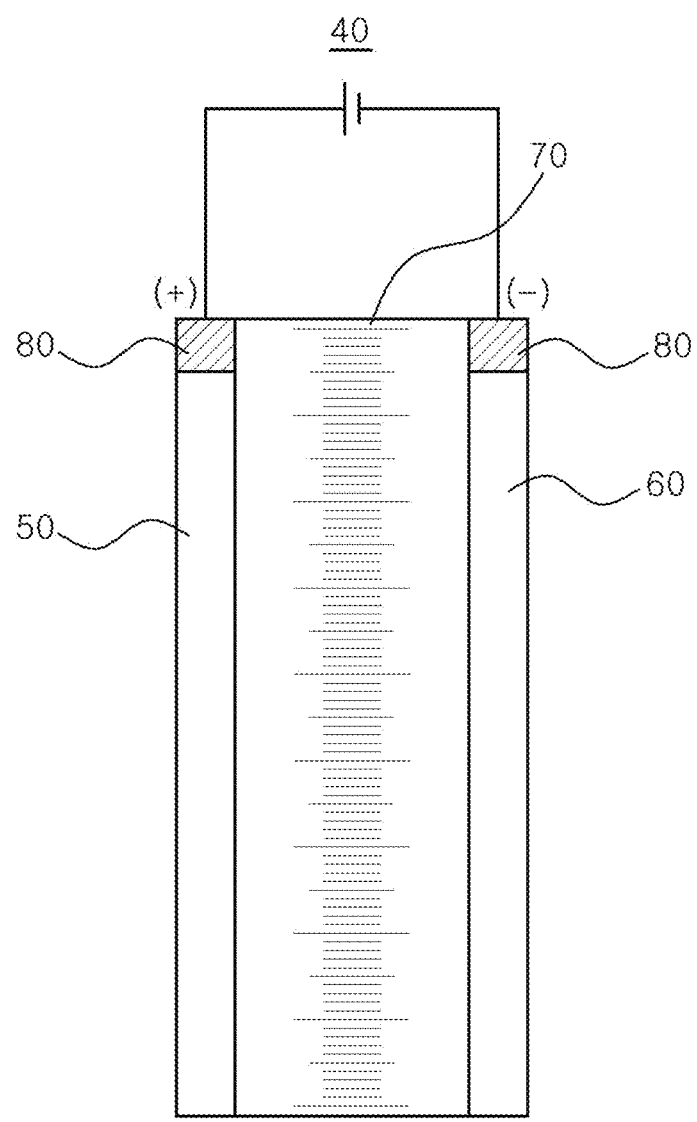
FIG. 5 is a diagram illustrating a height measuring plate that can be used with the cap-shaped stadiometer according to an embodiment of the present inventive concept.

FIGS. 4(a) and 4(b) are diagrams illustrating a measuring portion according to a preferred embodiment of the present inventive concept and a circuit diagram of the measuring portion, and FIG. 5 is a diagram illustrating a height measuring plate that can display height information through the portable stadiometer according to the present inventive concept.

Referring to FIGS. 4 and 5, FIG. 4(a) is a perspective view illustrating the sensors 31, 32, 33 and 34 of the measuring portion 30 in more detail, and FIG. 4(b) is a diagram illustrating an example where the measuring portion 30 comes into contact with the height measuring plate. The measuring portion 30 comprises upper sensors 31 and 32 and lower sensors 33 and 34, which are internally connected (e.g., within the measuring portion), forming a parallel structure or circuit with an applied electric current. Since the measuring sensors 31, 32, 33 and 34 have a parallel structure or circuit, the total resistance becomes R/2, causing the light-emitting diodes located at the top of the height measuring plate to emit light. However, if some sensors are not connected, failing to form a parallel structure, they have a resistance of R. In this case, the electric current cannot flow, and the light-emitting diodes cannot emit light. Therefore, when in contact with the height measuring plate, all the sensors 31, 32, 33 and 34 must be connected to the height measuring plate to ensure the flow of sufficient current, allowing the light-emitting diodes included in the height measuring plate to emit light. Since the sensors 31, 32, 33 and 34 make vertical contact with the height measuring plate, the connecting portion 20 is level with the ground, allowing for accurate height measurement.

Referring to FIG. 5, the sensors 31 and 33 come into contact with a positive pole 50 of the height measuring plate 40, and the other two sensors 32 come into contact with a negative pole 60, allowing the electric current to flow through the height measuring plate 40. The height measuring plate 40 is connected to the positive pole 50 and the negative pole 60 through the sensors 31, 32, 33 and 34, causing the light-emitting diodes 80 located at the top of the positive pole 50 and the negative pole 60 to emit light. When all the sensors 31, 32, 33 and 34 come into contact with the height measuring plate 40 to cause the light-emitting diodes 80 to emit light, the measuring rod 35 of the measuring portion 30 can come into contact with a height display portion 70 of the height measuring plate 40, allowing for display of height information.

Figure 6:
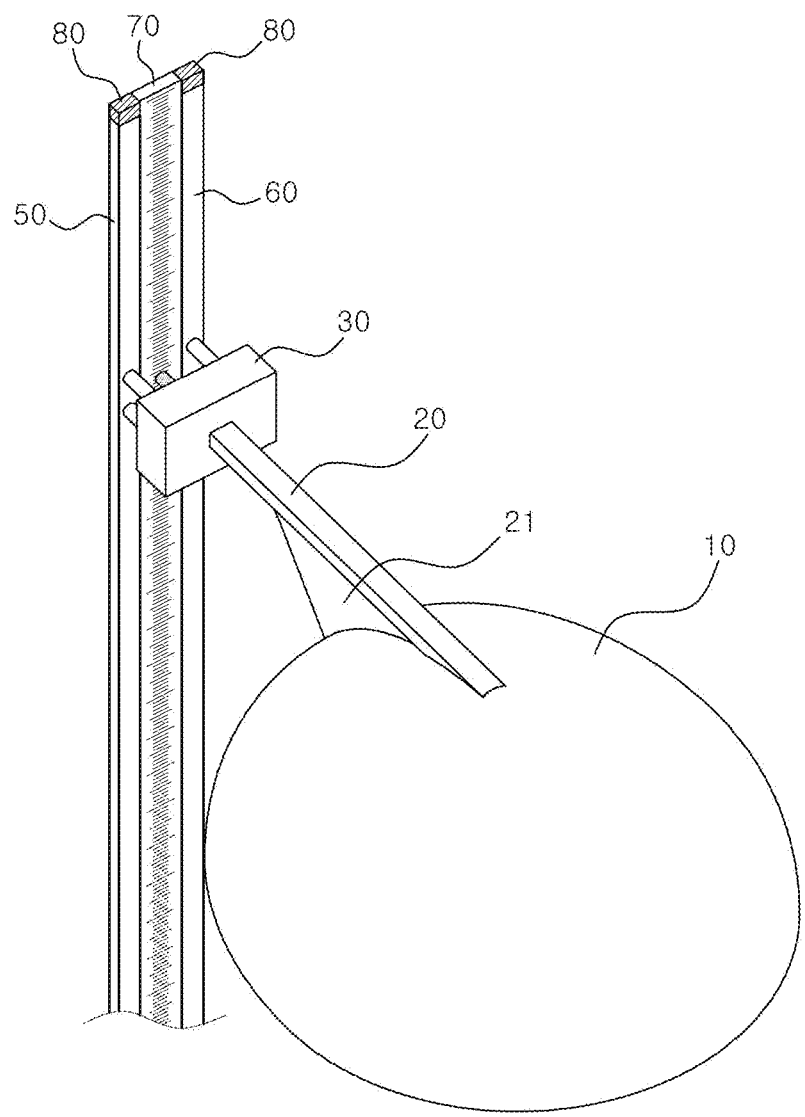
FIG. 6 is a diagram illustrating an example where the cap-shaped stadiometer according to an embodiment of the present inventive concept comes into contact with the height measuring plate.
Figure 7:
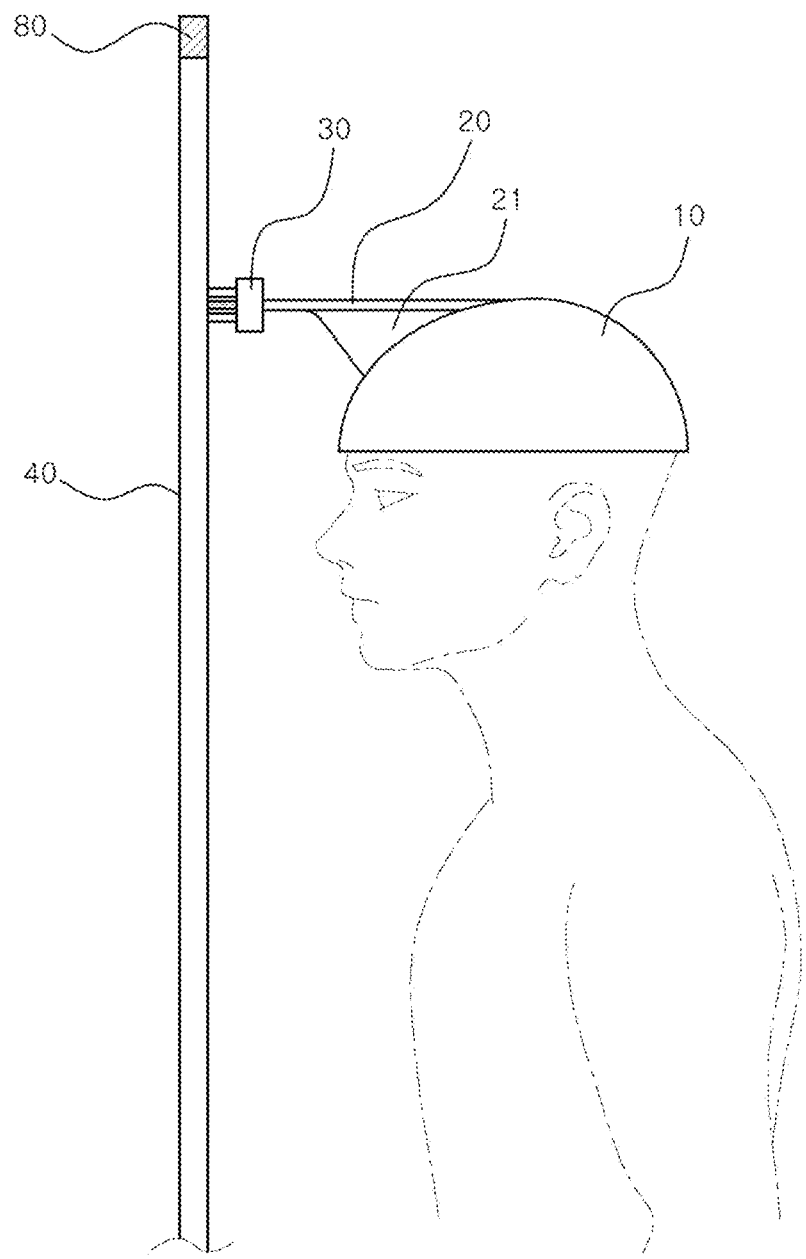
FIG. 7 is a diagram illustrating an example of measuring height by means of the cap-shaped stadiometer according to a preferred embodiment of the present inventive concept.

FIG. 6 is a diagram illustrating an example where the cap-shaped stadiometer according to an embodiment of the present inventive concept comes into contact with the height measuring plate, and FIG. 7 is a diagram illustrating an example of measuring height by means of the cap-shaped stadiometer.

Referring to FIGS. 6 and 7, after wearing the cap-shaped portable stadiometer, when the measuring portion 30 comes into contact with the height measuring plate 40 to be level with the ground, the measuring rod 35 of the measuring portion 30 comes into contact with the height display portion 70, allowing for measurement of height information.

Therefore, according to the present inventive concept as described above, since the portable stadiometer is in the form of a cap, it can be easily used for height measurement, similar to wearing a regular cap during measurement. This allows for convenient and accurate height measurement, even when alone. After wearing the portable stadiometer, when the measuring portion located at the front of the portable stadiometer comes into contact with a scaled height measuring plate, the sensors at each corner of the measuring portion react with the height measuring plate to cause the light-emitting diodes to emit light, making it possible to easily determine whether the portable stadiometer is level with the ground. Moreover, only when all the sensors in the measuring portion come into contact with the height measuring plate, the height measuring rod located in the center of the measuring portion comes into contact with the height measuring plate, allowing for easy and accurate height measurement.

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present inventive concept.

What is claimed is:

1. A stadiometer comprising:
 a cap portion adapted to be worn on a head of a user;
 a connecting portion having a first end coupled to the cap portion;
 a measuring portion coupled to a second end of the connecting portion, the measuring portion having:
  a plurality of sensors; and
  a measuring rod; and
 a height measuring plate contactable by the plurality of sensors and the measuring rod,
 wherein the plurality of sensors and the measuring rod are configured such that the measuring rod is configured to contact the height measuring plate when the height measuring plate is contacted by the plurality of sensors simultaneously,
 wherein ends of the plurality of sensors contactable by the height measuring plate are arranged within a common plane, wherein an end of the measuring rod contactable by the height measuring plate is arranged within the common plane, wherein the measuring rod is arranged between at least two of the plurality of sensors,
 wherein the measuring rod is located at the center of the measuring portion,
 wherein the height measuring plate includes a light configured to emit light when the height measuring plate is contacted by the plurality of sensors simultaneously,
 wherein the height measuring plate includes two poles contactable by at least one of the plurality of sensors, wherein the height measuring plate includes the light electrically connected to the two poles, wherein the two poles comprise:
  a first pole contactable by a first set of sensors of the plurality of sensors; and
  a second pole contactable by a second set of sensors of the plurality of sensors,
 wherein the plurality of sensors are electrically conductive and are electrically connected to each other in parallel,
 wherein the light is configured to emit the light in response to an applied current when the first pole and the second pole are simultaneously contacted by the first and second sets of sensors of the plurality of sensors.

2. The stadiometer of claim 1, wherein the measuring rod is a stamp type measuring rod having an end to which ink can be applied.

* * * * *